(12) United States Patent
Lee et al.

(10) Patent No.: US 9,701,699 B2
(45) Date of Patent: Jul. 11, 2017

(54) LIGAND COMPOUND, CATALYST SYSTEM FOR OLEFIN OLIGOMERIZATION, AND METHOD FOR OLEFIN OLIGOMERIZATION USING THE SAME

(71) Applicant: LG CHEM, LTD., Seoul (KR)

(72) Inventors: Yong Ho Lee, Daejeon (KR); Eun Ji Shin, Daejeon (KR); Seok Pil Sa, Daejeon (KR); Ki Soo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/892,679

(22) PCT Filed: Nov. 18, 2014

(86) PCT No.: PCT/KR2014/011076
§ 371 (c)(1),
(2) Date: Nov. 20, 2015

(87) PCT Pub. No.: WO2015/072810
PCT Pub. Date: May 21, 2015

(65) Prior Publication Data
US 2016/0304543 A1 Oct. 20, 2016

(30) Foreign Application Priority Data

Nov. 18, 2013 (KR) .................. 10-2013-0139994
Nov. 18, 2014 (KR) .................. 10-2014-0160781

(51) Int. Cl.
| | | |
|---|---|---|
| *C07F 9/50* | (2006.01) | |
| *C07F 9/46* | (2006.01) | |
| *C07C 2/36* | (2006.01) | |
| *C07C 211/54* | (2006.01) | |
| *B01J 31/14* | (2006.01) | |
| *B01J 31/18* | (2006.01) | |
| *C07C 2/26* | (2006.01) | |
| *C08F 110/02* | (2006.01) | |

(52) U.S. Cl.
CPC ........... *C07F 9/5022* (2013.01); *B01J 31/143* (2013.01); *B01J 31/188* (2013.01); *C07C 2/26* (2013.01); *C07C 2/36* (2013.01); *C07C 211/54* (2013.01); *C07F 9/46* (2013.01); *C08F 110/02* (2013.01); *B01J 2231/20* (2013.01); *B01J 2531/62* (2013.01); *C07C 2531/14* (2013.01); *C07C 2531/22* (2013.01)

(58) Field of Classification Search
None
See application file for complete search history.

(56) References Cited

U.S. PATENT DOCUMENTS 8,076,523 B2 12/2011 Bollmann et al.
2007/0232481 A1 10/2007 Zhang et al.

2008/0039600 A1* 2/2008 Bollmann .............. B01J 31/16
526/145
2010/0240847 A1 9/2010 Dixon et al.
2012/0199467 A1 8/2012 Gildenhuys et al.
2012/0310025 A1 12/2012 Wang et al.
2012/0316303 A1 12/2012 Hanton et al.

FOREIGN PATENT DOCUMENTS

| CN | 1651142 A | 8/2005 |
| CN | 101450326 A | 6/2009 |
| CN | 101687189 A | 3/2010 |

(Continued)

OTHER PUBLICATIONS

Kevin Blann et al.: "Ethylene tetramerisation: Subtle effects exhibited by N-substituted diphosphinoamine ligands", Journal of Catalysis 249 (2007) pp. 244-249.

(Continued)

*Primary Examiner* — Jafar Parsa
*Assistant Examiner* — Amy C Bonaparte
(74) *Attorney, Agent, or Firm* — Dentons US LLP

(57) ABSTRACT

This disclosure relates to a ligand compound, a catalyst system for olefin oligomerization, and a method for olefin oligomerization using the same. The catalyst system for olefin oligomerization according to the present invention has excellent catalytic activity, and yet, exhibits high selectivity to 1-hexene and 1-octene, thus enabling efficient preparation of alpha-olefin. The ligand compound is of the following Chemical Formula 1:

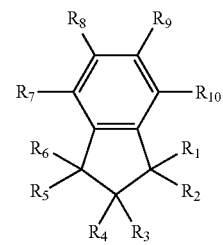

wherein at least one of R1 to R6 is a substituent of the following Chemical Formula 2:

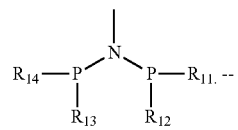

13 Claims, No Drawings

(56) References Cited

FOREIGN PATENT DOCUMENTS

| CN | 102666443 A | 9/2012 |
|---|---|---|
| CN | 103285926 A | 9/2013 |
| EP | 2520366 A1 | 11/2012 |
| JP | 2010-513412 A | 4/2010 |
| KR | 10-2012-0098711 A | 9/2012 |
| WO | 2008/077908 A1 | 7/2008 |
| WO | 2013-168098 A1 | 11/2013 |
| WO | 2013-168099 A1 | 11/2013 |

OTHER PUBLICATIONS

Sven Kuhlmann et al.: "N-substituted diphosphinoamines: Toward rational ligand design for the efficient tetramerization of ethylene", Journal of Catalysis 245 (2007) pp. 279-284.

Esna Killian et al.: "The use of bis(diphenylphosphino)amines with N-aryl functionalities in selective ethylene tri- and tetramerisation", Journal of Molecular Catalysis A: Chemical 270 (2007) pp. 214-218.

Anthea Carter et al.: "High activity ethylene trimerisation catalysts based on diphosphine ligands", ChemComm, 2002, pp. 858-859.

Kayan, et al.: "Aminophpsphine ligands: synthesis, coordination chemistry, and activity of their palladium(II) complexes in Heck and Suzuki cross-coupling reactions", XP019923288, Transition Metal Chemistry, vol. 36, No. 5, May 7, 2011, pp. 513-520.

* cited by examiner

LIGAND COMPOUND, CATALYST SYSTEM FOR OLEFIN OLIGOMERIZATION, AND METHOD FOR OLEFIN OLIGOMERIZATION USING THE SAME

This application is a National Stage Entry of International Application No. PCT/KR2014/011076, filed Nov. 18, 2014, and claims the benefit of and priority to Korean Application Nos. 10-2013-0139994, filed on Nov. 18, 2013 and 10-2014-0160781, filed on Nov. 18, 2014, all of which are hereby incorporated by reference in their entirety for all purposes as if fully set forth herein.

TECHNICAL FIELD

The present invention relates to a ligand compound, a catalysts system for olefin oligomerization, and a method for olefin oligomerization using the same.

BACKGROUND OF ART

Linear alpha-olefins, which are important materials used as comonomers, cleaners, lubricants, plasticizers and the like, are commercially widely used, and particularly, 1-hexene and 1-octene are used a lot as comonomers for controlling the density of polyethylene when preparing linear low-density polyethylene (LLDPE).

In the existing preparation process of LLDPE, ethylene is copolymerized with alpha-olefin comononers such as 1-hexene and 1-octene, so as to form branches in the polymer backbone to control the density.

Thus, there is a problem in that the cost of comonomers occupies a large part of production cost in the preparation of LLPDE having high comonomer content. There have been various attempts to solve the problem.

And, since alpha-olefins have various different application fields or market sizes according to the kind, a technology of selectively producing a specific olefin is commercially very important, and recently, a lot of studies are being progressed on the chromium catalyst technology for preparing 1-hexene or 1-octene with high selectivity through selective ethylene oligomerization.

The existing commercial preparation methods of 1-hexene or 1-octene include the SHOP process of Shell Chemical, the Ziegler process of Chevron Philips, and the like, whereby $C_{4-20}$ alpha-olefins with a wide distribution can be produced.

As a catalyst for trimerization of ethylene, a chromium-based catalyst using a ligand of the General Formula (R1)(R2)X—Y—X(R3)(R4) has been suggested. Wherein, X is phosphorous, arsenic or antimony, Y is a linking group such as —N(R5)-, and at least one of R1, R2, R3 and R4 has a polar or electron donating substituent.

And, as a ligand that exhibits catalytic activity to 1-hexene under catalytic conditions, studies have been progressed on o-ethylphenyl)$_2$PN(Me)P(o-ethylphenyl)$_2$, which does not have a polar substituent on at least one of R1, R2, R3 and R4 (*Chem. Commun.*, 2002, 858).

However, regarding the above explained ligand containing a heteroatom of the prior art, there is continued demand for consistently continued multimerization activity and high selectivity when preparing 1-octene or 1-hexene.

PRIOR ART DOCUMENTS

Non-Patent Documents

1. *Chem. Commun.*, 2002, 858

DETAILED DESCRIPTION OF THE INVENTION

Technical Problem

The object of the invention is to provide a novel ligand compound that can oligomerize olefins with high catalytic activity and selectivity, a catalyst system for olefin oligomerization comprising the same, and a method for olefin oligomerization using the same.

Technical Solution

The present invention provides a ligand compound represented by the following Chemical Formula 1:

[Chemical Formula 1]

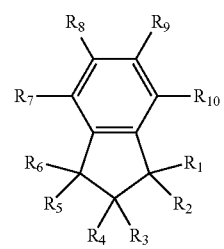

in the Chemical Formula 1,
at least one of $R_1$ to $R_6$ is a substituent represented by the following Chemical Formula 2,
the other $R_1$ to $R_6$, which are not represented by the following Chemical Formula 2, are independently hydrogen, a C1-20 alkyl group which may or may not contain at least one heteroatom, a C3-20 cycloalkyl group, a C6-20 aryl group, a C7-20 arylalkyl group, a C7-20 alkylaryl group, or a C3-30 heteroaryl group, provided that all of the other $R_1$ to $R_6$ which are not represented by the following Chemical Formula 2 cannot be hydrogen,
$R_7$ to $R_{10}$ are independently hydrogen, a C1-20 alkyl group which may or may not contain at least one heteroatom, a C3-20 cycloalkyl group, a C6-20 aryl group, a C7-20 arylalkyl group, a C7-20 alkylaryl group, or a C3-30 heteroaryl group, and two different neighboring groups of the $R_7$ to $R_{10}$ may be connected to each other to form a C6-20 aromatic ring,

[Chemical Formula 2]

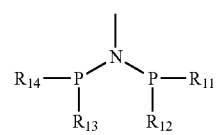

in the Chemical Formula 2,
$R_{11}$ to $R_{14}$ are independently a C1-20 alkyl group, a C2-20 alkenyl group, a C6-20 aryl group, a C7-20 arylalkyl group, a C7-20 alkylaryl group, or a C7-20 alkoxyaryl group.

The present invention also provides a catalyst system for olefin oligomerization comprising the ligand compound, a source of transition metal and a cocatalyst.

The present invention also provides a method for olefin oligomerization, comprising the step of multimerizing olefins in the presence of the catalyst system for olefin oligomerization.

Hereinafter, a ligand compound, a catalyst system for olefin oligomerization, and a method for olefin oligomerization according to specific embodiments of the invention will be explained in detail.

According to one embodiment of the invention, provided is a ligand compound represented by the following Chemical Formula 1:

[Chemical Formula 1]

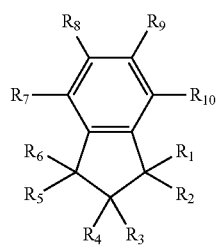

in the Chemical Formula 1, at least one of $R_1$ to $R_6$ is a substituent represented by the following Chemical Formula 2, the other $R_1$ to $R_6$, which are not represented by the following Chemical Formula 2, are independently hydrogen, a C1-20 alkyl group which may or may not contain at least one heteroatom, a C3-20 cycloalkyl group, a C6-20 aryl group, a C7-20 arylalkyl group, a C7-20 alkylaryl group, or a C3-30 heteroaryl group, provided that all of the other $R_1$ to $R_6$ which are not represented by the following Chemical Formula 2 cannot be hydrogen, $R_7$ to $R_{10}$ are independently hydrogen, a C1-20 alkyl group which may or may not contain at least one heteroatom, a C3-20 cycloalkyl group, a C6-20 aryl group, a C7-20 arylalkyl group, a C7-20 alkylaryl group, or a C3-30 heteroaryl group, and two different neighboring groups of the $R_7$ to $R_{10}$ may be connected to each other to form a C6-20 aromatic ring,

[Chemical Formula 2]

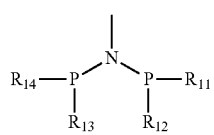

in the Chemical Formula 2, $R_{11}$ to $R_{14}$ are independently a C1-20 alkyl group, a C2-20 alkenyl group, a C6-20 aryl group, a C7-20 arylalkyl group, a C7-20 alkylaryl group, or a C7-20 alkoxyaryl group.

The inventors newly synthesized a previously unknown ligand compound, confirmed through experiments that if a substituent introduced in the ligand compound is appropriately controlled, the electronic, steric environment around a transition metal may be easily controlled, thus enabling olefin oligomerization with high catalytic activity and selectivity, and completed the invention.

Particularly, the ligand compound of the Chemical Formula 1 has a structure wherein a diphosphinoamine group represented by the Chemical Formula 2 is connected to an indenyl group, and thus, diphosphinoamine is substituted on an aliphatic group, thereby increasing selectivity to low carbon alpha-olefin such as 1-hexene and 1-octene compared to the case of being substituted on an aromatic group.

And, in case a substituent with appropriate steric hindrance is introduced in the atom adjacent to the carbon atom substituted with diphosphinoamine, selectivity to low carbon alpha-olefin may be increased, which is expected to result from the influence of an aliphatic group functioning as an electron donor, rather than a group with large electronegativity such as phenyl, on the reactivity of a complex compound wherein a phosphorous atom of diphosphinoamine is coordinated to chromium for increasing the selectivity.

And, in case diphosphinoamine is substituted on a cyclic group such as in the ligand compound of the Chemical Formula 1, since a plane formed by diphosphinoamine and a plane formed by the cyclic group are vertically oriented, and an appropriate substituent is introduced at a position adjacent to the disphosphinoamine-substituted position, lone pair electrons of the amine of a diphosphinoamine group are shielded, thus exhibiting higher selectivity. This is assumed to result from steric shielding of lone pair electrons of the N atom of the P—N bond vulnerable to Lewis acid or electrophile, and the resulting improvement in the stability of the ligand.

Hereinafter, each substituent in the Chemical Formula 1 will be explained in detail.

A C1-20 alkyl group includes a linear or branched alkyl group, and a C3-20 cycloalkyl group includes a C3-19 cycloalkyl group substituted with a C1-4 linear or branched alkyl group as well as a C3-20 cycloalkyl group.

An aryl group is preferably a C6-20 aromatic ring, and specific examples thereof may include phenyl, naphthyl, anthracenyl, pyridyl, dimethylanilinyl, anisolyl, and the like, but are not limited thereto.

An alkylaryl group means a C6-20 aryl group substituted with at least one linear or branched alkyl group, an arylalkyl group means a linear or branched alkyl group substituted with at least one C6-20 aryl group, and an alkoxyaryl group means a C6-20 aryl group substituted with at least one alkoxy group.

And, a heteroatom means N, O, F, S, or P, and a heteroaryl group means an aryl group containing at least one heteroatom.

And, a halogen group means fluorine (F), chlorine (Cl), bromine (Br), and iodine (I).

Wherein in the Chemical Formula 1, at least one of $R_1$ to $R_6$ that are not represented by the Chemical Formula 2 may be a C1-4 alkyl group, a C3-10 cycloalkyl group, a C6-10 aryl group, or a C7-15 arylalkyl group. Namely, in the Chemical Formula 1, at least one of $R_1$ to $R_6$ may be a substituent represented by the following Chemical Formula 2, and at least one of other $R_1$ to $R_6$ that are not represented by the Chemical Formula 2 may be above-described functional groups. As such, in case two or more substituents are introduced in the indenyl group of the Chemical Formula 1, compared to the case wherein a substituent is not introduced or only a diphosphinoamine group is introduced, in the vertically oriented diphosphinoamine group and cyclic group, the substituent of the cyclic group shields lone pair electrons at the N-position of diphosphinoamine from attack by Lewis acid or electrophile, thereby increasing structural stability of a disphosphinoamine ligand, thus increasing selectivity to low carbon alpha-olefin.

In addition, the substituents may have the effect of changing energy property of growth and dissociation step by ethylene insertion in the process of alpha-olefin production by olefin coordination.

And, $R_7$ to $R_{10}$ in the Chemical Formula 1 are independently hydrogen or a C1-20 alkyl group which may or may not contain at least one heteroatom, and two different neighboring groups of the $R_7$ to $R_{10}$ may be connected to each other to form a C6-20 aromatic ring.

And, $R_{11}$ to $R_{14}$ in the Chemical Formula 2 may be identical to each other, and preferably, may be phenyl.

And, representative examples of the ligand compound of the Chemical Formula 1 are as follows:

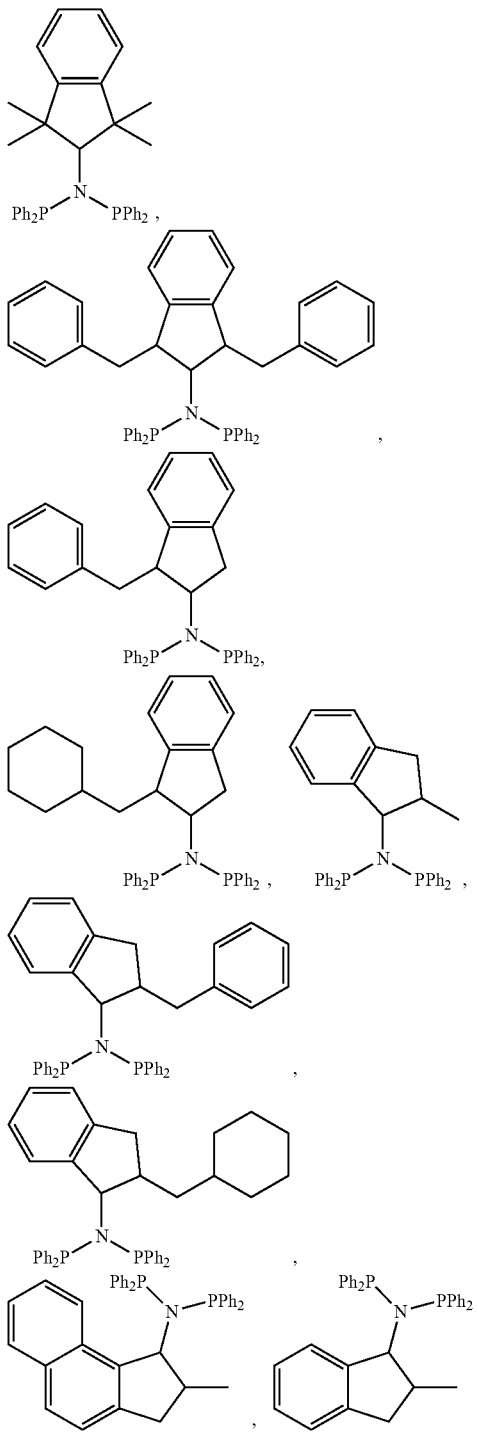

The compound represented by the Chemical Formula 1 includes all the possible optical isomers.

Meanwhile, the ligand compound represented by the Chemical Formula 1 may be synthesized by the following Reaction Formula 1, but is not limited thereto. A method for preparing the compound represented by the Chemical Formula 1 will be explained in detail in the examples below.

[Reaction Formula 1]

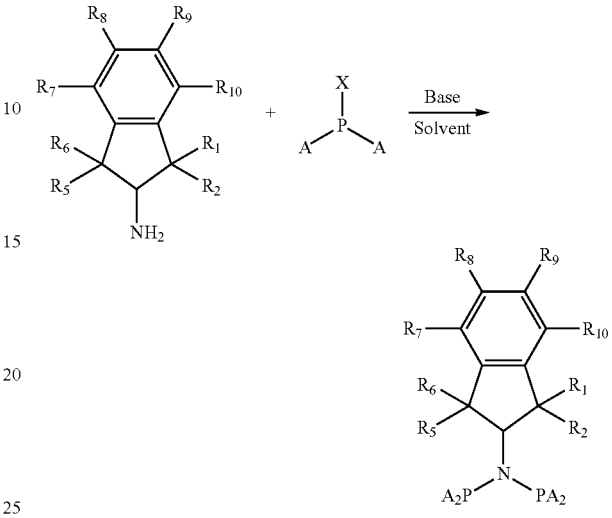

In the Reaction Formula 1, $R_1$ to $R_{10}$ are as defined in the Chemical Formula 1, A's are identical or different and independently are identical to the meanings of $R_{11}$ to $R_{14}$ in the Chemical Formula 2, and X is halogen.

Meanwhile, according to another embodiment, provided is a catalyst system for olefin oligomerization, comprising the ligand compound according to one embodiment, a source of transition metal and a cocatalyst.

As used herein, the term 'olefin oligomerization' means polymerization of a small number of olefins. When three olefins are polymerized, it is referred to as trimerization, when four olefins are polymerized, it is referred to as tetramerization, and the process of polymerization of a small number of olefins to form low molecular weight material is generally referred to as multimerization. Particularly, in the present invention, selective preparation of 1-hexene and 1-octene, main comonomers of LLDPE, from ethylene is referred to.

Selective olefin oligomerization is closely related to a catalyst system used. A catalyst system used for olefin oligomerization comprises a source of transition metal functioning as a main catalyst, and a cocatalyst, wherein the structure of the active catalyst may be changed according to the chemical structure of a ligand, thereby varying olefin selectivity.

As explained above, since the ligand compound according to one embodiment has a structure wherein a diphosphinoamine group represented by the Chemical Formula 2 is connected to an indenyl group, a catalyst system comprising the same may easily control the electronic/steric environment around a transition metal, thereby enabling olefin oligomerization with high catalytic activity and selectivity.

The source of transition metal functions as a main catalyst, and preferably, is at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III) hexafluoro-2,4-pentanedionate, and chromium(III)acetate hydroxide.

The cocatalyst is an organic metal compound including a Group 13 metal, and is not specifically limited as long as it can be used for olefin multimerization in the presence of a transition metal catalyst. Specifically, as the cocatalyst, at least one selected from the group consisting of the compounds represented by the following Chemical Formulae 3 to 5 may be used.

$$-[Al(R_{15})-O]c- \qquad \text{[Chemical Formula 3]}$$

in the Chemical Formula 3, $R_{15}$'s are identical or different, and are independently a halogen radical, a C1-20 hydrocarbyl radical, or a C1-20 hydrocarbyl radical substituted with halogen, and c is an integer of 2 or more, $$D(R_{16})_3 \qquad \text{[Chemical Formula 4]}$$

in the Chemical Formula 4,

D is aluminum or boron, $R_{16}$'s are identical or different, and are independently hydrogen, halogen, a C1-20 hydrocarbyl or a C1-20 hydrocaryl substituted with halogen, $$[L-H]^+[Q(E)_4]^- \qquad \text{[Chemical Formula 5]}$$

in the Chemical Formula 5,

L is neutral Lewis base, $[L-H]^+$ is Bronsted acid, Q is $Br^{3+}$ or $Al^{3+}$, and E's are independently a $C_{6-20}$ aryl group or a $C_{1-20}$ alkyl group, unsubstituted or substituted with at least one selected from the group consisting of halogen, $C_{1-20}$ hydrocarbyl, a $C_{1-20}$ alkoxy and phenoxy.

Examples of the compound represented by the Chemical Formula 3 may include modified methylaluminoxane (MMAO), methylaluminoxane (MAO), ethylaluminoxane, isobutylaluminoxane, butylaluminoxane, and the like.

Examples of the alkyl metal compound represented by the Chemical Formula 4 may include trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tollylaluminum, dimethylaluminummethoxide, dimethylaluminumethoxide, trimethylboron, triethylboron, triisobutylboron, tripropylboron, tributylboron, and the like.

Examples of the compound represented by the Chemical Formula 5 may include triethylammonium tetraphenylboron, tributylammonium tetraphenylboron, trimethylammonium tetraphenylboron, tripropylammonium tetraphenylboron, trimethylammonium tetra(p-tollyl)boron, tripropylammonium tetra(p-tollyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tollyl)aluminum, tripropylammonium tetra(p-tollyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylboron, triphenylcarbonium tetraphenylaluminum, triphenylcarbonium tetra (p-trifluoromethylphenyl)boron, triphenylcarbonium tetrapentafluorophenylboron, and the like.

As the cocatalyst of the catalyst system for olefin oligomerization, aluminoxane may be preferably used, and more preferably, methylaluminoxane (MAO) or modified methylaluminoxane (MMAO) may be used.

The catalyst system for olefin oligomerization may have a mole ratio of the ligand compound:source of transition metal:cocatalyst of about 1:1:1 to about 10:1:10,000, preferably about 1:1:100 to about 5:1:3,000, so as to increase selectivity to linear alpha-olefin and multimerization activity, but is not limited thereto.

In the catalyst system for olefin oligomerization comprising the ligand compound represented by the Chemical Formula 1, a source of transition metal and cocatalyst, the three components may be added simultaneously or sequentially in a random order in a suitable solvent in the absence or presence of monomers, and be obtained as an active catalyst. The active solvent may include heptane, toluene, cyclohexane, methylcyclohexane, 1-hexene, diethylether, tetrahydrofuran, acetonitrile, dichloromethane, chloroform, chlorobenzene, methanol, acetone and the like, but is not limited thereto.

Meanwhile, according to still another embodiment of the invention, provided is a method for olefin oligomerization, comprising the step of multimerizing olefins in the presence of the catalyst system for olefin oligomerization. If the catalyst system for olefin oligomerizatoin according to the present invention is used, a method for olefin oligomerization with improved activity and selectivity may be provided. The olefin may be preferably ethylene.

The olefin oligomerization according to the present invention may be conducted as a homogeneous liquid phase reaction, a slurry reaction wherein a catalyst system is not dissolved in part or in whole, a two-phase liquid/liquid reaction, or a bulk phase reaction or a gas phase reaction wherein product olefin acts as a main medium, in the absence or presence of an inert solvent, using the catalyst system for olefin oligomerization and a common device and contact technology, and the homogeneous liquid phase reaction is preferable.

The olefin oligomerization may be conducted in any inert solvent that does not react with a catalyst compound and an activator. The suitable inert solvent may include benzene, toluene, xylene, cumene, heptane, cyclohexane, methylcyclohexane, methylcyclopentane, hexane, pentane, butane, isobutane and the like, but is not limited thereto. Wherein, the solvent may be treated with a small amount of alkylaluminum to remove a small amount of water or air acting as a catalyst poison, before use.

The olefin oligomerization may be conducted at a temperature of about 5° C. to about 200° C., preferably about 30° C. to about 150° C. And, the olefin oligomerization may be conducted at a pressure of about 1 bar to about 300 bar, preferably about 2 bar to about 150 bar.

According to one example of the invention, it was confirmed that as a result of oligomerizing ethylene with a catalyst system using the ligand compound represented by the Chemical Formula 1 as a ligand, 1-hexene and 1-octene can be selectively synthesized.

Advantageous Effects

By using a catalyst system comprising the ligand compound according to the present invention, ethylene may be oligomerized with higher catalytic activity and selectivity compared to the existing catalyst system.

DETAILED DESCRIPTION OF THE EMBODIMENTS

Hereinafter, the present invention will be explained in detail with reference to the following examples. However, these examples are only to illustrate the invention and the scope of the invention is not limited thereto.

<Synthesis of Ligand Compound>

All the reactions were progressed using Schlenk technique or a Glove box under argon atmosphere. The synthesized compounds were analyzed by $^1$H (500 MHz) and $^{31}$P(202 MHz) NMR spectra using a Varian 500 MHz spectrometer. Shift was expressed in ppm, downfield from TMS, with a residual solvent peak as a reference. A phosphorous probe was calibrated with aqueous $H_3PO_4$.

Example 1

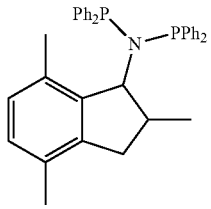

p-Xylene (6.2 g, 58 mmol) and $AlCl_3$ (15.47 g, 116 mmol) were introduced in a schlenk flask, and an argon condition was made. Dry DCM (100 mL) was introduced, followed by cooling to −78° C., and then, 2-bromo-2-methylpropionyl bromide (13.6 g, 59.12 mmol) was slowly introduced, followed by temperature elevation to room temperature, and then, stirring for 16 hours. After the stirring, the mixture was slowly quenched with water, and worked up with water/DCM. An organic layer was collected and dried, and then, the obtained 2,4,7-trimethyl-2,3-dihydro-1H-inden-1-one was used in the subsequent reaction.

A dried 250 mL schlenk flask was vacuum dried for more than 1 hour, and then, 1.74 g of the above synthesized 2,4,7-trimethyl-2,3-dihydro-1H-inden-1-one (10 mmol) was introduced into the flask. 25 mL of a 2M NH3 ethanol solution (50 mmol) was introduced in the flask, and under inert atmosphere, 5.7 mL of titanium(IV) isopropoxide (19 mmol) was slowly added dropwise to the flask while stirring in a water bath. After the introduction, the mixture was stirred overnight at room temperature.

In another schlenk flask, 0.57 g of sodium borohydride (15 mmol) was introduced, followed by vacuum drying for more than 1 hour, and then, replacing with Ar, and the above reacting mixture was added dropwise through a cannula in an ice bath. After the introduction, the temperature of the mixture was slowly raised to a room temperature, and then, the mixture was stirred for more than 4 hours. In an ice bath, an ammonium hydroxide aqueous solution (50 mmol) was slowly added dropwise to the reaction mixture, and the mixture was quenched, extracted with CHCl3 to remove remaining moisture of the organic layer, and then, the solvent was removed under vacuum decompression to obtain 1.4 g of 2,4,7-trimethyl-2,3-dihydro-1H-inden-1-amine (7.9 mmol) in the oily state, which was used in the subsequent reaction.

Under argon, 2,4,7-trimethyl-2,3-dihydro-1H-inden-1-amine and triethylamine (3~10 equivalents) were dissolved in dichloromethane (40~80 mL). While the flask was immersed in a water bath, chlorodiphenylphosphine (2 equivalents) was slowly introduced, and the mixture was stirred overnight. The solvent was removed under vacuum, THF was added and sufficiently stirred, and triethylammonium chloride salt was removed with an air-free glass filter. The solvent was removed in the filtrate to obtain N-(diphenylphosphino)-1,1-diphenyl-N-(2,4,7-trimethyl-2,3-dihydro-1H-inden-1-yl)phosphinamine.

$^{31}$P NMR (202 MHz, CDCl$_3$): 48.6 (br s), 52.4 (br s)

Example 2

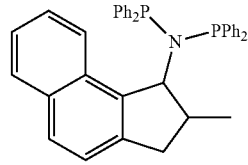

2-methyl-2,3-dihydro-1H-cyclopenta[a]naphthalen-1-amine was obtained by the same method as Example 1, except using naphthalene instead of p-xylene, and in the subsequent reaction, N-(diphenylphosphino)-N-(2-methyl-2,3-dihydro-1H-cyclopenta[a]naphthalen-1-yl)-1,1-diphenylphosphinamine was obtained in the oily state.

$^{31}$P NMR (202 MHz, CDCl$_3$): 46.1 (br s), 53.9 (br s)

Comparative Example 1

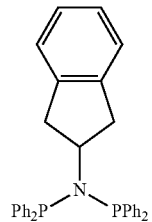

Under argon, 2,3-dihydro-1H-inden-2-amine and triethylamine (3~10 equivalents) were dissolved in dichloromethane (40~80 mL). While the flask was immersed in a water bath, chlorodiphenylphosphine (2 equivalents) were slowly introduced, and the mixture was stirred overnight. The solvent was removed under vacuum, and then, THF was added, the mixture was sufficiently stirred, and triethylammonium chloride salt was removed with an air-free glass filter. The solvent was removed in the filtrate to obtain N-(2,3-dihydro-1H-inden-2-yl)-N-(diphenylphosphino)-1,1-diphenylphosphinamine in a white solid state.

$^1$H NMR (500 MHz, CDCl$_3$): 2.60 (m, 2H), 3.34 (m, 2H), 4.40 (m, 1H), 6.90-7.7 (m, Ar, 2H); $^{31}$P (202 MHz, CDCl$_3$): 49.4 (br s)

Comparative Example 2

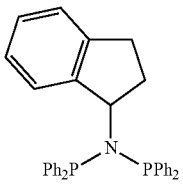

N-(2,3-dihydro-1H-inden-1-yl)-N-(diphenylphosphino)-1,1-diphenylphosphinamine was obtained in a solid state by the same method as Example 1, except using 2,3-dihydro-1H-inden-1-amine instead of 2,3-dihydro-1H-inden-2-amine.

$^1$H NMR (500 MHz, CDCl$_3$): 2.00 (1H, m), 2.21 (1H, m), 2.67 (1H, m), 3.30 (1H, 2m), 5.17 (1H, m), 6.47 (1H, d), 6.99 (1H, t), 7.00-7.45 (22H, m); $^{31}$P (202 MHz, CDCl$_3$): 50.7 (br s)

Comparative Example 3

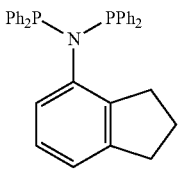

N-(2,3-dihydro-1H-inden-4-yl)-N-(diphenylphosphino)-1,1-diphenylphosphinamine was obtained in a solid state by the same method as Example 1, except using 2,3-dihydro-1H-inden-4-amine instead of 2,3-dihydro-1H-inden-2-amine.

$^{31}$P NMR (202 MHz, CDCl$_3$): 63.5 (s)

<Olefin Oligomerization>

Experimental Example 1

(Step 1)

Under argon gas, Cr(acac)$_3$(17.5 mg, 0.05 mmol) and the ligand prepared in the Example 1 (0.05 mmol) were introduced in a flask, toluene (10 mL) was added, and the mixture was stirred to prepare a 5 mM solution.

(Step 2)

A 600 mL Parr reactor was prepared, vacuum was applied at 120° C. for 2 hours, and then, the inside was replaced with argon, and the temperature was decreased to 45° C. And, 350 mL of toluene and 2.2 mL of MAO (toluene solution, Al/Cr=300) were introduced, and 2 mL of the 5 mM solution (10 umol) was introduced in the reactor. The mixture was stirred at 500 rpm for 2 minutes, and then, a valve of an ethylene line adjusted to 45 bar was opened to fill the inside of the reactor with ethylene, and the mixture was stirred at 500 rpm for 15 minutes. The ethylene line valve was closed, the reactor was cooled to 0° C. with a dry ice/acetone bath, and then, non-reacted ethylene was slowly vented, and 0.5 mL of nonane (GC internal standard) was introduced. After stirring for 10 seconds, 2 mL of the liquid part of the reactor was taken and quenched with water, the organic part was filtered with a PTFE syringe filter to make a GC sample. The GC sample was analyzed with GC.

(Step 3)

To the remaining reaction solution, 400 mL of ethanol/HCl (10 vol %) was added, and the mixture was stirred and filtered to obtain polymer. The obtained polymer was dried overnight in a 65° C. vacuum oven, and the weight was measured.

Experimental Example 2

(Step 1)

Under argon gas, Cr(acac)$_3$(17.5 mg, 0.05 mmol) and the ligand prepared in the Example 1 (0.05 mmol) were introduced in a flask, 100 ml of cyclohexane was added, and the mixture was stirred to prepare a 0.5 mM (based on Cr) solution.

(Step 2)

A 600 mL Parr reactor was prepared, vacuum was applied at 120° C. for 2 hours, and then, the inside was replaced with argon, and the temperature was decreased to 60° C. And, 175 ml of methylcyclohexane and 2 ml of MMAO (isoheptane solution, Al/Cr=1200) were introduced, and 5 mL of the 0.5 mM solution (2.5 umol) was introduced in the reactor. The mixture was stirred at 500 rpm, and then, a valve of an ethylene line adjusted to 60 bar was opened to fill the inside of the reactor with ethylene, followed by removing heat to 60° C., and stiffing at 500 rpm for 15 minutes. The ethylene line valve was closed, the reactor was cooled to 0° C. with a dry ice/acetone bath, and then, non-reacted ethylene was slowly vented, and 0.5 ml of nonane (GC internal standard) was introduced. After stiffing for 10 seconds, 2 mL of the liquid part of the reactor was taken and quenched with water, the organic part was filtered with a PTFE syringe filter to make a GC sample, which was analyzed by GC.

(Step 3)

To the remaining reaction solution, 400 mL of ethanol/HCl (10 vol %) was added, and the mixture was stirred and filtered to obtain polymer. The obtained polymer was dried overnight in a 65° C. vacuum oven, and the weight was measured.

Experimental Example 3

The experiment was conducted by the same method as Experimental Example 2, except using the ligand prepared in Example 2 instead of the ligand prepared in Example 1.

Comparative Experimental Example 1

The experiment was conducted by the same method as Experimental Example 1, except using the ligand of Comparative Example 1 instead of the ligand of Example 1.

Comparative Experimental Example 2

The experiment was conducted by the same method as Experimental Example 1, except using the ligand of Comparative Example 1 instead of the ligand of Experimental Example 1, and using cyclohexane instead of toluene in the step 2.

Comparative Experimental Example 3

The experiment was conducted by the same method as Experimental Example 1, except using the ligand compound of Comparative Example 1 instead of the ligand compound of Experimental Example 1, using dichloromethane instead of toluene in the step 1, and using 350 mL of cyclohexane and 1.7 mL of MMAO (isoheptane solution, Al/Cr=300) instead of toluene and MAO (toluene solution, Al/Cr=300) in the step 2.

Comparative Experimental Example 4

The experiment was conducted by the same method as Experimental Example 1, except using the ligand compound of Comparative Example 1 instead of the ligand compound of Experimental Example 1, using 350 mL of cyclohexane and 3.4 mL of MMAO (isoheptane solution, Al/Cr=1200) instead of toluene and MAO (toluene solution, Al/Cr=300) in the step 2, and using 1 mL (5 umol) of the 5 mM solution instead of 2 mL (10 umol).

Comparative Experimental Example 5

The experiment was conducted by the same method as Experimental Example 1, except using the ligand compound of Comparative Example 2 instead of the ligand compound of Example 1.

Comparative Experimental Example 6

The experiment was conducted by the same method as Experimental Example 1, except using the ligand compound of Comparative Example 2 instead of the ligand compound of Example 1, using 350 mL of cyclohexane and 3.4 mL of MMAO (isoheptane solution, Al/Cr=1200) instead of toluene and MAO (toluene solution, Al/Cr=300) in the step 2, and using 1 mL (5 umol) of the 5 mM solution instead of 2 mL (10 umol).

Comparative Experimental Example 7

The experiment was conducted by the same method as Experimental Example 1, except using the ligand compound of Comparative Example 2 instead of the ligand compound of Example 1, and using 4.4 mL of MAO (toluene solution, Al/Cr=600).

Comparative Experimental Example 8

(Step 1)
Under argon gas, $Cr(acac)_3$ (17.5 mg, 0.05 mmol) and the ligand prepared in the Comparative Example 2 (0.05 mmol) were introduced in a flask, 100 ml of cyclohexane was added, and the mixture was stirred to prepare a 0.5 mM (based on Cr) solution.

(Step 2)
A 600 mL Parr reactor was prepared, vacuum was applied at 120° C. for 2 hours, and then, the inside was replaced with argon, and the temperature was decreased to 60° C. And, 175 ml of methylcyclohexane and 2 ml of MMAO (isoheptane solution, Al/Cr=1200) were introduced, and 5 mL of the 0.5 mM solution (2.5 umol) was introduced in the reactor. The mixture was stirred at 500 rpm, and then, a valve of an ethylene line adjusted to 60 bar was opened to fill the inside of the reactor with ethylene, followed by removing heat to 60° C., and stirring at 500 rpm for 15 minutes. The ethylene line valve was closed, the reactor was cooled to 0° C. with a dry ice/acetone bath, and then, non-reacted ethylene was slowly vented, and 0.5 mL of nonane (GC internal standard) was introduced. After stiffing for 10 seconds, 2 mL of the liquid part of the reactor was taken and quenched with water, the organic part was filtered with a PTFE syringe filter and subjected to GC analysis.

(Step 3)
To the remaining reaction solution, 400 mL of ethanol/HCl (10 vol %) was added, and the mixture was stirred and filtered to obtain polymer. The obtained polymer was dried overnight in a 65° C. vacuum oven, and the weight was measured.

Comparative Experimental Example 9

The experiment was conducted by the same method as Comparative Experimental Example 8, except using the ligand compound of Comparative Example 3 instead of the ligand compound of Comparative Example 2.

The results of Experimental Examples 1 to 3 and Comparative Experimental Examples 1 to 9 are shown in the following Table 1.

TABLE 1

|  | Solid alpha-olefin ($>1-C_{40}$; wt %) | Selectivity (wt %) | | | | Activity (kg/mol/Cr/hr) |
|---|---|---|---|---|---|---|
|  |  | 1-hexene | 1-octene | $1-C_{10}$ to $1-C_{40}$ | sum |  |
| Experimental Example 1 | 0.1 | 21.2 | 70.0 | 5.0 | 96.2 | 10,200 |
| Experimental Example 2 | 0.1 | 31.5 | 62.4 | 4.3 | 98.2 | 98,000 |
| Experimental Example 3 | 0.3 | 27.9 | 65.3 | 4.8 | 98.0 | 112,000 |
| Comparative Experimental Example 1 | 1.1 | 13.7 | 64.3 | 12.4 | 90.4 | 6,400 |
| Comparative Experimental Example 2 | 1.2 | 13.3 | 63.8 | 13.6 | 90.7 | 10,500 |
| Comparative Experimental Example 3 | 25.9 | 14.9 | 51.9 | 20.8 | 87.6 | 1,200 |
| Comparative Experimental Example 4 | 1.8 | 9.9 | 63.1 | 16.5 | 89.5 | 10,500 |
| Comparative Experimental Example 5 | 1.1 | 19.7 | 68.3 | 4.8 | 92.8 | 6,200 |

TABLE 1-continued

|  | Solid alpha-olefin (>1-$C_{40}$; wt %) | Selectivity (wt %) | | | | Activity (kg/mol/Cr/hr) |
|---|---|---|---|---|---|---|
|  |  | 1-hexene | 1-octene | 1-$C_{10}$ to 1-$C_{40}$ | sum |  |
| Comparative Experimental Example 6 | 0.07 | 16.4 | 70.9 | 5.1 | 92.4 | 18,000 |
| Comparative Experimental Example 7 | 0.54 | 12.9 | 74.1 | 5.3 | 92.3 | 18,700 |
| Comparative Experimental Example 8 | 0.1 | 25.6 | 64.9 | 3.4 | 93.9 | 70,000 |
| Comparative Experimental Example 9 | 0.7 | 18.4 | 62.1 | 8.3 | 88.8 | 119,000 |

As shown in the Table 1, it was confirmed that Experimental Examples using the compounds according to the present invention exhibited very high multimerization activity, produced a very small amount of solid by-products, and had remarkably improved selectivity to alpha-olefin (1-hexene and 1-octene).

The invention claimed is:

1. A ligand compound of Chemical Formula 1:

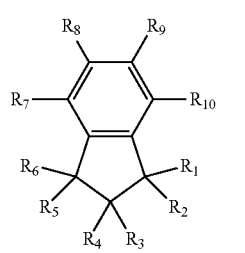

[Chemical Formula 1]

wherein in the Chemical Formula 1, at least one of $R_1$ to $R_6$ is a substituent of Chemical Formula 2, the other $R_1$ to $R_6$, which are not the substituent of the Chemical Formula 2, are independently hydrogen, a C1-20 alkyl group which may or may not contain at least one heteroatom, a C3-20 cycloalkyl group, a C6-20 aryl group, a C7-20 arylalkyl group, a C7-20 alkylaryl group, or a C5-30 heteroaryl group, provided that all the other $R_1$ to $R_6$ which are not the substituent of the Chemical Formula 2 cannot be hydrogen, $R_7$ to $R_{10}$ are independently hydrogen, a C1-20 alkyl group which may or may not contain at least one heteroatom, a C3-20 cycloalkyl group, a C6-20 aryl group, a C7-20 arylalkyl group, a C7-20 alkylaryl group, or a C5-30 heteroaryl group, or two different neighboring groups of the $R_7$ to $R_{10}$ may be connected to each other to form a C6-20 aromatic ring,

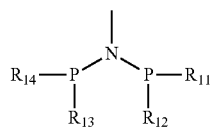

[Chemical Formula 2]

wherein in the Chemical Formula 2, $R_{11}$ to $R_{14}$ are independently a C1-20 alkyl group, a C2-20 alkenyl group, a C6-20 aryl group, a C7-20 arylalkyl group, a C7-20 alkylaryl group, or a C7-20 alkoxyaryl group.

2. The ligand compound according to claim 1, wherein in the Chemical Formula 1, at least one of $R_1$ to $R_6$ that are not the substituent of the Chemical Formula 2 is a C1-4 alkyl group, a C3-10 cycloalkyl group, a C6-10 aryl group, or a C7-15 arylalkyl group.

3. The ligand compound according to claim 1, wherein $R_7$ to $R_{10}$ in the Chemical Formula 1 are independently hydrogen or a C1-20 alkyl group which may or may not contain at least one heteroatom, or two different neighboring groups of the $R_7$ to $R_{10}$ may be connected to each other to form a C6-20 aromatic ring.

4. The ligand compound according to claim 1, wherein $R_{11}$ to $R_{14}$ in the Chemical Formula 2 are identical to each other.

5. The ligand compound according to claim 1, wherein $R_{11}$ to $R_{14}$ in the Chemical Formula 2 are phenyl.

6. The ligand compound according to claim 1, wherein the compound of the Chemical Formula 1 is selected from the group consisting of

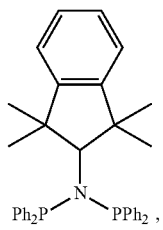

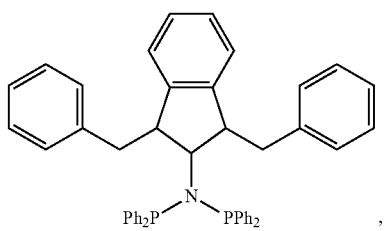

,

-continued

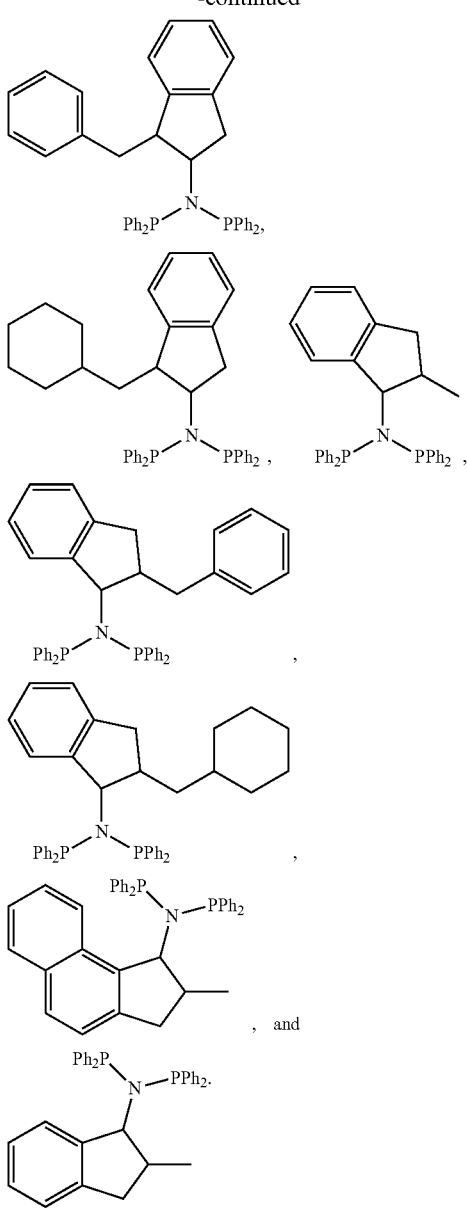

7. A catalyst system for olefin oligomerization comprising the ligand compound according to claim 1, a source of transition metal and a cocatalyst.

8. The catalyst system according to claim 7, wherein the source of transition metal is at least one selected from the group consisting of chromium(III)acetylacetonate, tris(tetrahydrofuran)chromium trichloride, chromium(III)-2-ethylhexanoate, chromium(III)tris(2,2,6,6-tetramethyl-3,5-heptanedionate), chromium(III)benzoylacetonate, chromium (III)hexafluoro-2,4-pentanedionate, and chromium(III) acetate hydroxide.

9. The catalyst system according to claim 7, wherein the cocatalyst is at least one compound selected from the group consisting of a compound of Chemical Formula 3, a compound of Chemical Formula 4, and a compound of Chemical Formula to 5:

—[Al($R_{15}$)—O]$c$-    [Chemical Formula 3]

wherein in the Chemical Formula 3, $R_{15}$'s are identical or different, and are independently a halogen radical, a C1-20 hydrocarbyl radical, or a C1-20 hydrocarbyl radical substituted with halogen, and c is an integer of 2 or more, D($R_{16}$)$_3$    [Chemical Formula 4]

wherein in the Chemical Formula 4,

D is aluminum or boron, $R_{16}$'s are identical or different, and are independently hydrogen, halogen, a C1-20 hydrocarbyl or a C1-20 hydrocarbyl substituted with halogen,

[L-H]$^+$[Q(E)$_4$]$^-$    [Chemical Formula 5]

wherein in the Chemical Formula 5,

L is a neutral Lewis base, [L-H]$^+$ is a Bronsted acid, Q is B$^{3+}$ or Al$^{3+}$, and E's are independently a $C_{6-20}$ aryl group or a $C_{1-20}$ alkyl group, unsubstituted or substituted with at least one group selected from the group consisting of halogen, a $C_{1-20}$ hydrocarbyl, an alkoxy and a phenoxy group.

10. A method for olefin oligomerization, comprising the step of multimerizing olefins in the presence of the catalyst system for olefin oligomerization of claim 7.

11. The method for olefin oligomerization according to claim 10, wherein the olefin is ethylene.

12. The method for olefin oligomerization according to claim 10, wherein the multimerization temperature is 5 to 200° C.

13. The method for olefin oligomerization according to claim 10, wherein the multimerization pressure is 1 to 300 bar.

* * * * *